United States Patent [19]

Paul, Jr.

[11] Patent Number: 5,399,165
[45] Date of Patent: Mar. 21, 1995

[54] LOCKABLE CONNECTOR, A DRAINAGE CATHETER UTILIZING THE CONNECTOR, AND METHOD OF USE

[75] Inventor: Ram H. Paul, Jr., Bloomington, Ind.

[73] Assignee: Cook Incorporated, Bloomington, Ind.

[21] Appl. No.: 259,353

[22] Filed: Jun. 13, 1994

Related U.S. Application Data

[63] Continuation of Ser. No. 10,655, Jan. 28, 1993, abandoned.

[51] Int. Cl.⁶ ............................................. A61M 37/00
[52] U.S. Cl. ...................................... 604/95; 604/174; 604/178; 604/280
[58] Field of Search ................................ 604/174, 178

[56] References Cited

U.S. PATENT DOCUMENTS

| | | |
|---|---|---|
| 1,207,479 | 12/1916 | Bisgaard . |
| 3,119,392 | 1/1964 | Zeiss . |
| 3,394,954 | 7/1968 | Sarns . |
| 3,554,580 | 1/1971 | Goyke . |
| 3,924,633 | 12/1975 | Cook et al. . |
| 4,586,923 | 5/1986 | Gould et al. .......... 604/95 |
| 4,592,749 | 6/1986 | Ebling et al. . |
| 4,643,720 | 2/1987 | Lanciano . |
| 4,740,195 | 4/1988 | Lanciano . |
| 4,869,719 | 9/1989 | Hogan . |
| 4,963,129 | 10/1990 | Rusch . |
| 4,969,879 | 11/1990 | Lichte . |
| 5,041,085 | 8/1991 | Osborne et al. ....... 604/95 |

OTHER PUBLICATIONS

"Wills–Oglesby Percutaneous Gastrostomy Set", Cook Incorporated, Bloomington, Ind., 1984.
"Cook–Cope Type Loop Drainage Sets", Cook Incorporated, Bloomington, Ind., 1983.
Roll et al., "Simplification of the Cope Loop Catheter", Seminars in Interventional Radiology, vol. 4, No. 1, Mar. 1987, p. 46.
"Catheters, stents, and retrieval devices for Non-vascular Intervention", Medi–tech Incorporated, Watertown, Mass., 1989.

Primary Examiner—C. Fred Rosenbaum
Assistant Examiner—Perry E. Van Over
Attorney, Agent, or Firm—Richard J. Godlewski

[57] ABSTRACT

A drainage catheter with a distal member end that is lockable in a desired loop configuration for retaining the catheter in a body cavity such as the bladder. The lockable drainage catheter includes a flexible tension member for drawing the distal member end into a loop. The tension member extends through a lockable connector positioned about the proximal member end. The lockable connector includes a resilient material sleeve with a sleeve passage extending longitudinally therethrough for positioning the tension member therein. The sleeve is positioned in a passage of the connector adjacent a channel wherein a pivotedly attached lever is positioned. When the lever is pivoted toward the connector into a fixed position, a cam surface of the lever compresses the sleeve and locks thereabout to maintain the loop formed in the distal member end.

25 Claims, 4 Drawing Sheets

FIG. 9

LOCKABLE CONNECTOR, A DRAINAGE CATHETER UTILIZING THE CONNECTOR, AND METHOD OF USE

This is a continuatioin of application Ser. No. 08/010,655, filed on Jan. 28, 1993, now abandoned.

TECHNICAL FIELD

This invention relates to catheters and particularly to a drainage catheter having a lockable connector for drawing and maintaining the distal end into a desired configuration.

BACKGROUND OF THE INVENTION

Suprapubic catheterization of the bladder is used to drain the bladder after surgery or when the genitourinary system is plugged by an obstruction. Other percutaneously inserted catheters are also used to drain the kidney or biliary system as well as to drain abscesses, other sites of fluid collection, and other viscera. Still other percutaneously inserted catheters are gastrostomy feeding tubes.

These catheters are typically introduced into the patient by means of a large hypodermic needle or trocar, which pierces the abdominal wall. A wire guide is inserted through the needle and then removed. The catheter tube with a stiffening cannula positioned therein is then passed over the wire guide into the cavity. The cannula and wire guide are withdrawn, leaving the catheter in the desired cavity. With respect to the bladder, the advantage of this technique is that irrigation and infection of the urinary tract is minimized. However, one problem with these catheters is that the catheter can be easily pulled out by movement of the body or by the emptying of, for example, the bladder. Another problem is that side ports at the distal end of the catheter may be inadvertently drawn into the abdominal cavity, creating the potential for severe infections.

Various catheters have been developed with so-called pigtail loops at their distal ends for ensuring drainage of the cavity and preventing accidental removal therefrom. The pigtail loop is tightened by pulling on the proximal end of a flexible tension member, which extends through the catheter. The proximal end of this tension member is held in place by any one of a number of retention means. In one case, the proximal end of the flexible tension member is held in place by axially placing a hollow cap into or over the proximal end of the catheter tube, thus trapping the flexible tension member of which the protruding end may then be cut. A problem with this catheter design is that once the protruding end of the flexible tension member is cut, the hollow cap may slip or be inadvertently removed. As a result, the shortened flexible tension member moves distally, releases the pigtail, and is either difficult or impossible to retrieve.

In another case, the flexible tension member is trapped between two or more hollow tubes, one of which is slidably inserted axially into the other. A short length of the flexible member is generally left hanging from the catheter tube so that if the flexible tension member becomes loose, it may be retightened. Alternatively, an external sleeve is slid over the flexible tension member protruding from the side of the catheter tube of which the flexible tension member is then wound around and tied about the sleeve.

Although well-suited for its intended purpose, this catheter design leaves the flexible tension member exposed at the proximal end of the catheter. As a result, a physician must grasp and pull on the flexible tension member to secure or tie it about the proximal catheter end. In addition, a patient can untie the exposed flexible tension member and require the assistance of hospital personnel to retie the member. Furthermore, when the flexible tension member is inadvertently released, the retaining loop at the distal end is released with the possibility of the catheter being withdrawn from the patient.

In yet another case, the proximal end of a flexible tension member is bent and secured between two cooperating locking members, one of which is laterally movable across the path of the flexible tension member. A problem with this catheter design is that the locking members bend or deform the flexible tension member. As a result, the locking members may break or cut the flexible tension member, thereby inadvertently releasing the distally positioned loop and allowing the withdrawal of the catheter from the patient.

SUMMARY OF THE INVENTION

The foregoing problems are solved and a technical advance is achieved in an illustrative lockable, drainage catheter connector having a lever pivotedly connected in a channel of the connector body for moving a cam surface at one end of the lever between a locked position and an unlocked position. In the locked position, the cam surface engages a tension member, which is drawn into the connector channel and past the cam surface to configure the distal end of a drainage catheter into a desired configuration. The pivotedly connected lever has a fixed position and a disengaged position for moving the cam surface between the locked position and the unlocked position, respectively. The connector body has a first body passage extending therethrough for draining fluid received from a hollow elongated member of the drainage catheter, which is inserted percutaneously into a patient. Communicating with the drainage passage, the connector body channel receives the tension member positioned through the elongated member and drainage passage for drawing the distal end of the elongated member into a desired configuration such as a closed loop or pigtail.

The drainage catheter connector further comprises a resilient material sleeve communicating with the connector channel for compression by the cam surface of the lever. The sleeve has a passage extending therethrough that communicates with the first body passage and channel for passage of the tension member therethrough. Advantageously, the resilient material sleeve provides a fluid-tight seal between the first body passage and connector channel, while still allowing engagement of the tension member with the cam surface of the lever.

The drainage catheter connector also comprises a second body passage having an external opening for external passage of the tension member from the connector when the distal end of the drainage catheter is being drawn into the desired configuration. This second body passage communicates with the channel in which the resilient material sleeve is positioned and communicates with the connector channel for compression by the cam surface.

The lever of the drainage catheter connector advantageously has a recess formed therein for receiving a corresponding projection extending from the channel when the lever is positioned in the fixed position. Alternatively, the connector channel has a recess formed therein for receiving a corresponding projection extending from the lever when the lever is positioned in the fixed position. When in the fixed position, the lever or the connector channel further comprises another recess formed therein in which the lever can be externally engaged to release the lever from the fixed position in the connector channel.

The drainage catheter connector further includes an elongated member for insertion into a patient, which has a distal member formed into a desired configuration. The elongated member also has a proximal member end connected to the connector body and a passage extending longitudinally therethrough for communication with the connector drainage passage. Fluid is drained from the patient through the percutaneously inserted catheter into a fluid collection system. The tension member extends along the elongated member and is positioned for drawing the distal member end into the desired configuration. As previously suggested, the tension member has at least one end that communicates with the cam surface of the lever for drawing the distal member end into the desired configuration.

The elongated member of the catheter includes first and second ports proximate the distal member end that communicate with the member passage. The tension member advantageously extends through these ports and member passage for drawing the distal member end into the desired configuration.

In an enhancement to the lockable, drainage catheter connector, the connector channel further comprises a projection extending therein and proximate the cam surface when in the locked position for advantageously minimizing the need for a mating recess and projection on or in the lever and connector channel when the lever is in the fixed position.

In another enhancement to the lockable, drainage catheter connector of the present invention, the channel further comprises a compression projection extending therein for compression of the resilient material sleeve. A contour in the cam surface of the lever enhances compression of the resilient material sleeve about the channel compression projection.

The drainage catheter of the present invention includes a hollow elongated member for insertion into a patient. The distal member end of the hollow elongated member is formed to be positioned into a desired configuration such as a closed loop or pigtail. The drainage catheter also includes a lockable connector connected to the proximal end of the hollow member and has a first connector passage extending therethrough and a channel communicating with the first connector passage. Pivotedly connected in the channel of the connector is a lever having a cam surface proximate one end thereof for engaging a drawable tension member when the cam surface is in a locked position. The lever has a fixed position and a disengaged position for moving the cam surface between a locked position and an unlocked position. The drainage catheter also comprises tension means extending along the elongated member and into the lockable connector for drawing the distal member end into the desired configuration. The tension member has at least one end extending to the connector channel for communication with and engagement of the cam surface.

The method of percutaneously draining fluid from the cavity of a patient with a medical device such as the heretofore described drainage catheter and lockable connector includes the steps of percutaneously inserting the distal member end of the elongated member into the cavity of a patient and moving the drawable tension means past the cam surface to reconfigure the distal member end of the catheter into the desired configuration. The cam surface of the lever is positioned in the locked position, and a fluid collection system is connected to the lockable connector.

The method further comprises providing a resilient material sleeve communicating with the channel of the connector and passing the drawable tension means through a passage extending through the sleeve. When in the locked positioned, the cam surface compresses the resilient material sleeve to form a fluid-tight seal.

DETAILED DESCRIPTION

Figure 1:
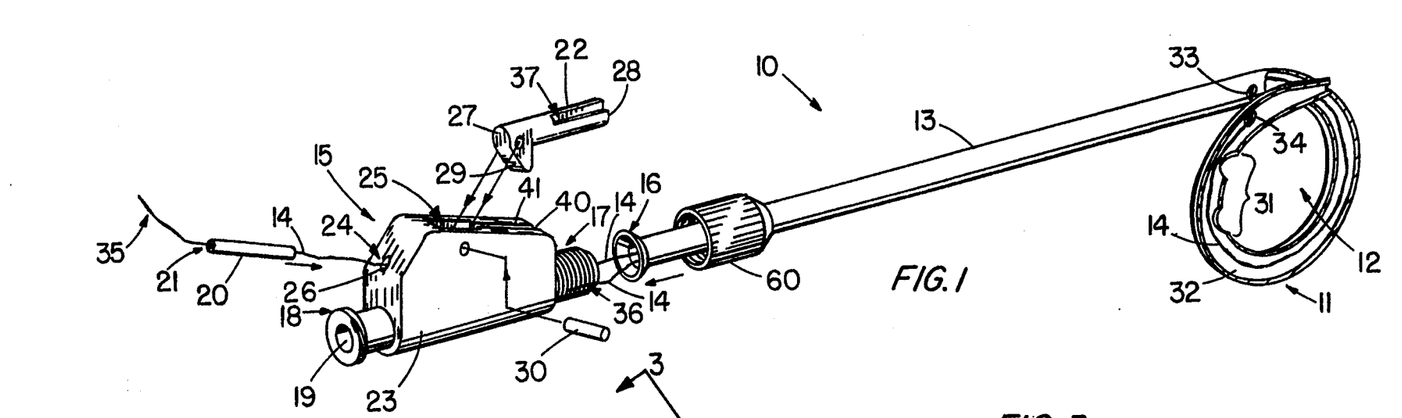
FIG. 1 depicts a pictorial view of the medical device of the present invention.

FIG. 1 depicts a pictorial view of an illustrative medical device such as cam-locked drainage catheter 10 prior to percutaneous insertion into, for example, the bladder of a patient. The drainage catheter is depicted with distal member end 11 drawn into desired configuration 12 such as a pigtail or loop. However, the distal member end assumes a straight configuration with a stiffening cannula during a well-known percutaneous technique for introducing the drainage catheter over a wire guide and into the bladder through the abdominal wall of a patient. The wire guide and stiffening cannula are removed from the patient, leaving the drainage catheter in place for providing fluid flow from the bladder to a well-known fluid collection system (not shown) such as a proximally extending piece of tubing and a plastic collection bag. Drainage catheter 10 comprises elongated member 13 with distal member end 11 for retaining the elongated member in the bladder and tension member 14 such as commercially available flexible filament suture material for extending therealong and drawing the distal member end into the desired loop configuration. Drainage catheter 10 further comprises lockable connector 15 that is positioned about and connected to flared, proximal member end 16 of the elongated member for fixing the position of the tension member with respect to the elongated member, thereby maintaining the desired loop configuration.

Lockable connector 15 includes connector body 23 with distal connector end 17; proximal connector end 18; and first body passage 19 extending longitudinally therethrough for communicating with member passage 32 of the elongated member and providing continuous fluid flow through the drainage catheter. Lockable connector 15 further includes second body passage 24 and channel 25 that communicate with the first body passage. A resilient material sleeve 20 with sleeve passage 21 extending longitudinally therethrough is positioned in the second body passage for extending tension member 14 therethrough. Second body passage 24 includes external opening 26 so that tension member 14 exits the connector proximally for grasping the tension member and drawing distal member end 11 into a pigtail or loop configuration. Lever 22 of the connector includes ends 27 and 28 and cam surface 29 positioned proximate end 27. The lever is pivotedly interconnected about end 27 to connector body 23 by pivot pin 30.

As also depicted in FIG. 1, elongated member 13 includes member passage 32 extending longitudinally between distal member end 11 and proximal member end 16 and plurality 31 of drainage ports positioned proximate distal member end 11. Elongated member 13 further includes ports 33 and 34 positioned proximate distal member end 11 and communicating with member passage 32. Tension member 14 extends along the member passage and through ports 33 and 34. Ports 33 and 34 are spaced apart a predetermined length equal to the circumference of the desirable loop configuration.

Tension member 14 includes end 35 which is positioned through lockable connector 15 and extends therefrom for grasping and drawing the tension member to form the desired loop configuration. Tension member 14 further includes end 36, which is attached to body 23 of the lockable connector about threaded distal connector end 17 and well-known connector cap 60. Alternatively, end 22 is attached to proximal member end 16.

Figure 2:
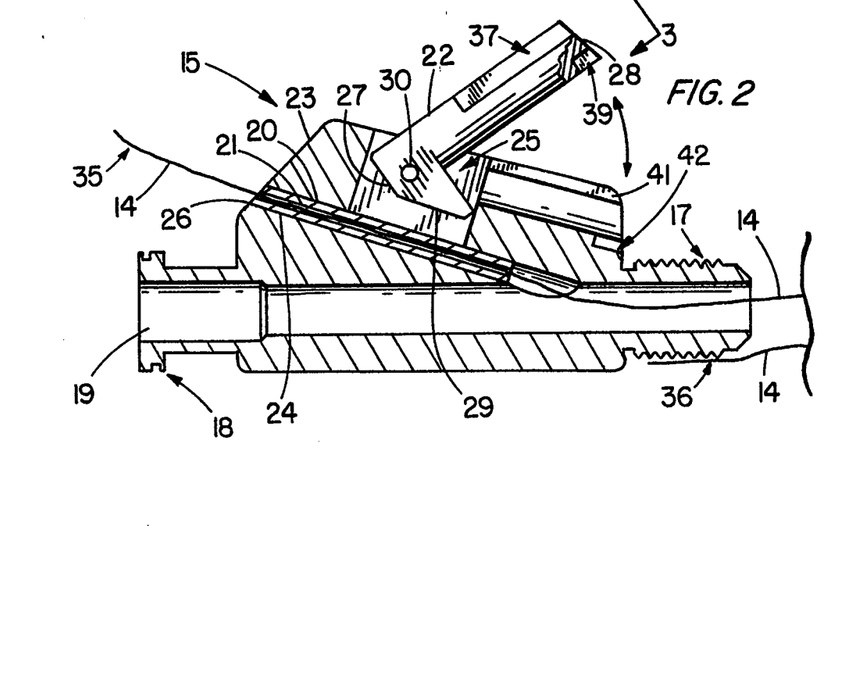
FIG. 2 depicts a partially sectioned longitudinal view of the lockable drainage catheter connector of FIG. 1 with the connector lever in a disengaged position.

FIG. 2 depicts a partially sectioned longitudinal view of lockable connector 15 with lever 22 in a disengaged or movable position. With end 28 of lever 22 pivoted away from connector body 23, cam surface 29 is in an unlocked position not engaging tension member 14 in resilient material sleeve 20.

Figure 3:
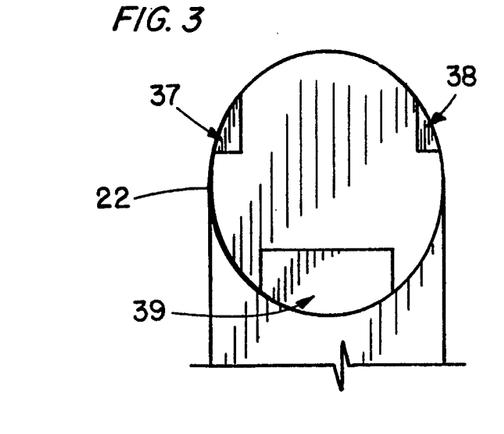
FIG. 3 depicts an end view of the connector lever of FIG. 2 taken along the line 3—3.

FIG. 3 depicts an end view of the connector lever 22 of FIG. 2 taken along the line 3—3 in a disengaged or movable position. Lever 22 includes longitudinal recesses 37 and 38 for positioning therein and engaging respective corresponding or mating projections 40 and 41 extending longitudinally along channel 25 to maintain the lever in the fixed position.

Figure 4:
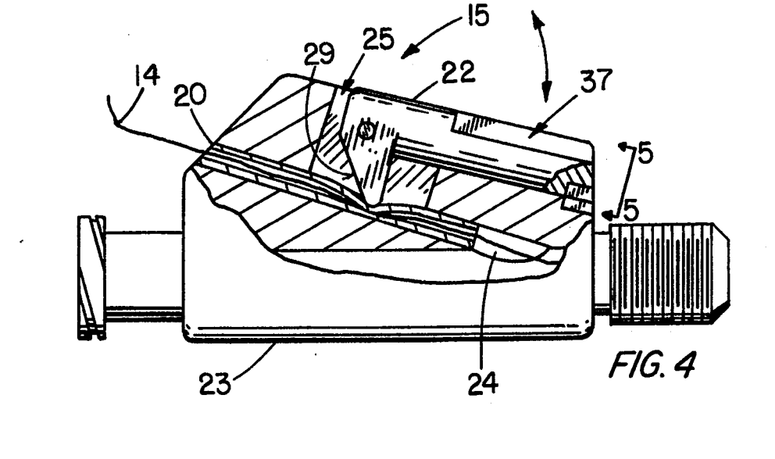
FIG. 4 depicts a partially sectioned longitudinal view of the connector of FIG. 1 with the connector lever in a fixed position.

FIG. 4 depicts a partially sectioned, longitudinal view of connector 15 of FIG. 1 with lever 22 in the fixed position. Cam surface 29 of the lever is in a locked position compressing against resilient material sleeve 20 and engaging tension member 14 positioned through the sleeve. The engaged tension member maintains distal member end in the desired configuration. The compressed sleeve also forms a fluid-tight seal and prevents draining fluid from entering second body passage 24 and channel 25.

Figure 5:
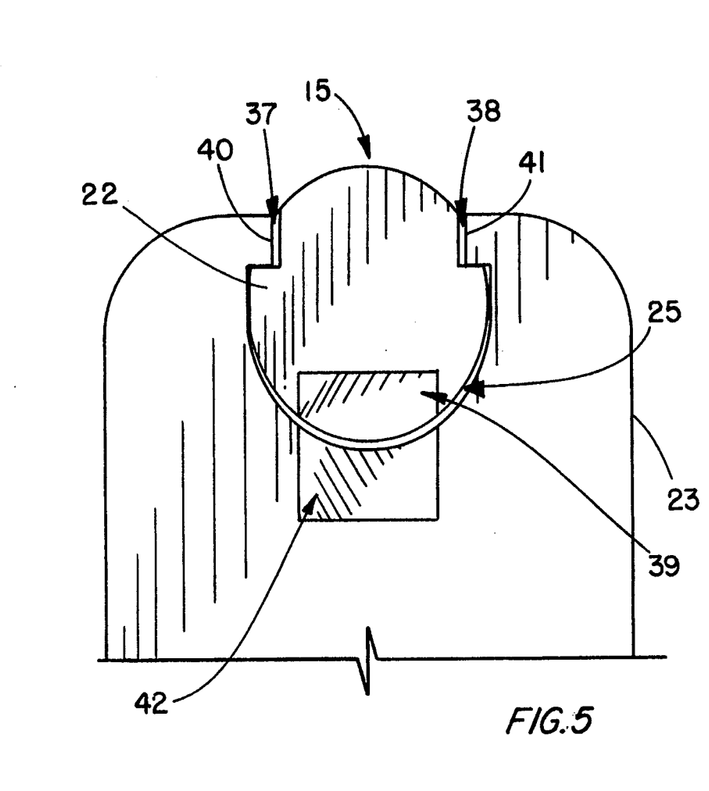
FIG. 5 depicts an end view of the lockable drainage catheter connector of FIG. 4 taken along the line 5—5.

FIG. 5 depicts end view of connector 15 of FIG. 4 taken along the line 5—5 with lever 22 in channel 25 in the fixed position. Channel 25 includes longitudinal projections 40 and 41 for extending in and engaging respective or mating recesses 37 and 38. Channel 25 further includes end recess 42 for cooperating with end recess 39 of the lever to externally engage the lever and move it to a disengaged or movable position.

Figure 9:
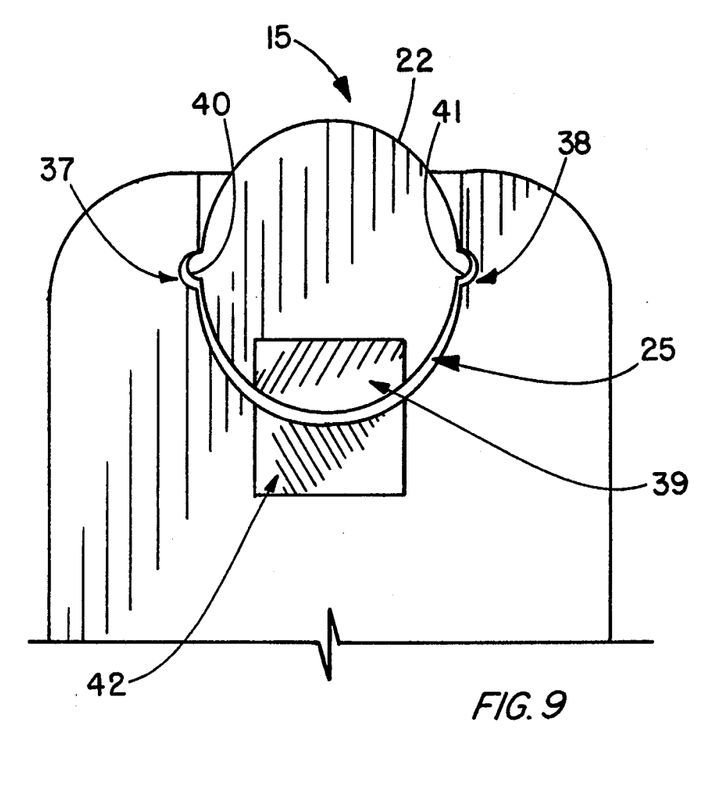
FIG. 9 depicts an end view of the connector of FIG. 5 in which the longitudinal recesses and projections of the channel and lever have been reversed.

FIG. 9 depicts an end view of connector 15 of FIG. 5 in which longitudinal recesses 37 and 38 are formed in channel 25 and respective longitudinal projections 40 and 41 extend from lever 22. This is an alternative configuration from that depicted in FIG. 5.

Lockable connector 15, for example, is formed of a 1.588" long and 0.312" thick piece of a rigid, medical grade polymer such as polyester-polybutylate-terepthalate. Passage 19 has a minimum inside diameter of 0.140". Distal connector end 17 is 0.338" in length and includes ¼-32 external threads positioned thereabout for a length of approximately 0.300". Proximal connector end 18 includes well-known male Luer lock connector fitting, which is a flange 0.300" in diameter and 0.055" long with a 10 pitch double thread positioned thereabout. Connector body 23 is approximately 0.650" wide at its widest point proximate external opening 26. The connector body tapers down to a 0.406" width for an axial distance of 0.265" toward the proximal connector end and is 0.468" wide for an axial distance of 0.735" toward the threaded distal connector end. Sharp corners on the body are rounded to a 0.050" radius. Distal connector end includes a 45° chamfer. Channel 25 has a bottom cut to communicate with second body passage 24 and extends longitudinally along the body passage for a length of 0.295". Channel 25 is approximately 0.135" wide and 0.238" deep at the portion of the channel positioned 0.357" proximal to the 0.468" wide step on the connector body adjacent the distal connector end. The distal portion of channel 25 has a rounded cross-sectional shape with a maximum diameter of 0.140" and a depth of 0.128". Body passage 24 has a 0.060" diameter and is centered 0.184" below the axis of the widest point of the connector body. Projections 40 and 41 extend laterally for a width of 0.010" apiece and are 0.125" long and 0.033" high. The connector body includes a 0.075" radius on either side of the channel. End recess 42 is 0.038" deep and 0.075" wide. A 0.042" diameter hole is drilled through the connector body and lever for positioning pivot pin 30 therethrough. Lever 22 is formed of a piece of polyester-polybutylate-terepthalate material approximately 0.635" long, 0.265" wide, and 0.125" thick. The lever has a generally rounded cross-section with an outside diameter of 0.125" for a length of 0.497". Recess 39 is 0.075" long and 0.038" wide proximate end 28. End 27 positioned proximate cam surface 29 has a 34° taper beginning 0.114" from the top of the lever. Sharp corners of the lever are rounded to a 0.015" radius. The lockable connector is attached to the proximal end of the elongated member in a well-known flared fitting manner with threadable connector cap 60 and medical grade adhesive. Threadable connector cap 60 comprises, for example, Delrin material and has a 0.240" minimum outside diameter, a 0.350" maximum outside diameter, a 0.250" radius positioned therebetween, a portion of straight knurling positioned on the outside surface thereof, and a plurality of ¼-32 internal threads for mating with the external threads of the distal connector end. The inside diameter of the connector cap includes a stepped reduction for facilitating a secure, flared fitting connection to the elongated member. The elongated member comprises a polyurethane material tube approximately 40 cm long. Elongated member 13 has an 8.5 French outside diameter and is attached to the lockable connector using a connector cap with a 0.117" minimum inside diameter; for a 10.2 French outside diameter member, a 0.140" minimum inside diameter connector cap is needed; for a 12.0 French outside diameter member, a 0.158" minimum inside diameter cap is needed; and for a 14.0 French outside diameter member, a 0.191" inside diameter cap is needed.

A method of using drainage catheter 10 for percutaneously draining fluid from, for example, the bladder of a patient is performed by inserting distal member end 11 into the bladder. This step is typically performed by first inserting a thin-wall needle with a stylet inserted therein through the abdominal wall and into the bladder using a well-known technique. The stylet is removed, and a wire guide is inserted through the needle into the bladder. The needle is removed, leaving the wire guide in place. A dilator is commonly used over the wire guide to increase the size of the puncture site. Drainage catheter 10 with a stiffening cannula inserted therein is inserted over the wire guide into the bladder. Next, tension member 14 is moved or drawn proximally past cam surface 29 to form distal member end 11 into desired loop or pigtail configuration 12. Cam surface 29 is then positioned in the locked position, thereby engaging and compressing resilient material sleeve 20 with tension member 14 positioned therein. When lever 22 is in the fixed position, the cam surface and sleeve form a fluidtight seal thereabout. Finally, proximal connector end 18 is connected to a fluid collection system (not shown) for continuously draining the bladder of a patient.

Figure 6:
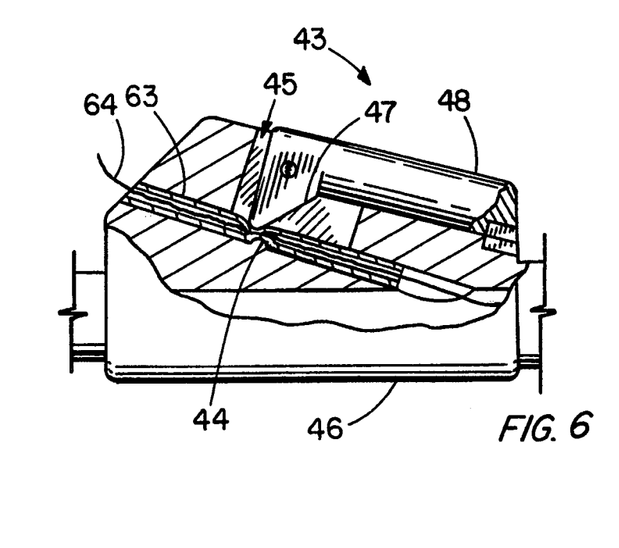
FIG. 6 depicts an enhancement to the medical device of FIG. 1.

FIG. 6 depicts a partially sectioned, longitudinal view of enhanced lockable connector 43, which represents another aspect of connector 15 of FIGS. 1-5, but includes projection 44 extending into the bottom of channel 45 of connector body 46 just distal of cam surface 47 when in the locked position. Cam surface 47 is just proximal of the lock projection when in the locked position, thereby compressing against resilient material tube 63 and engaging tension member 64. As a result, no longitudinal recesses and corresponding projections are required in the channel and lever to maintain the lever in the fixed position.

Figure 7:
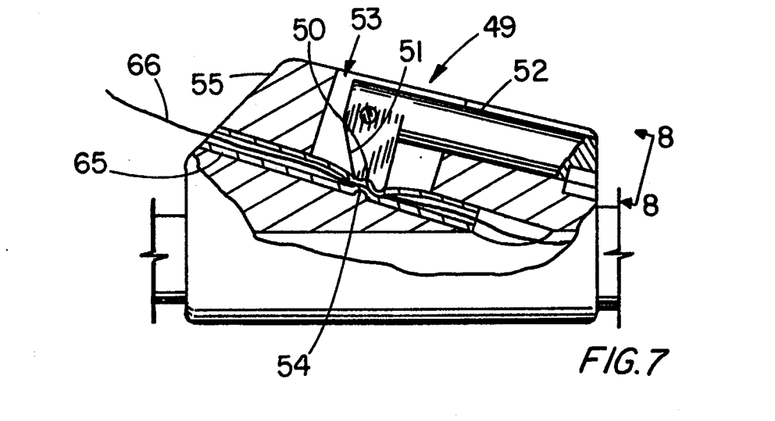
FIG. 7 depicts another enhancement to the medical device of FIG. 1.

FIG. 7 depicts a partially sectioned, longitudinal view of another enhanced lockable connector 49, which represents still another aspect of connector 15 of FIGS. 1-5, but includes contour 50 on cam surface 51 positioned proximally on lever 52. Channel 53 of connector body 55 includes compression projection 54 positioned proximate cam surface 51 for cooperating with and compressing resilient material sleeve 65 against the contour when lever 52 is in the fixed position. As a result, tension member 66 is more securely engaged between the contour and compression projection.

Figure 8:
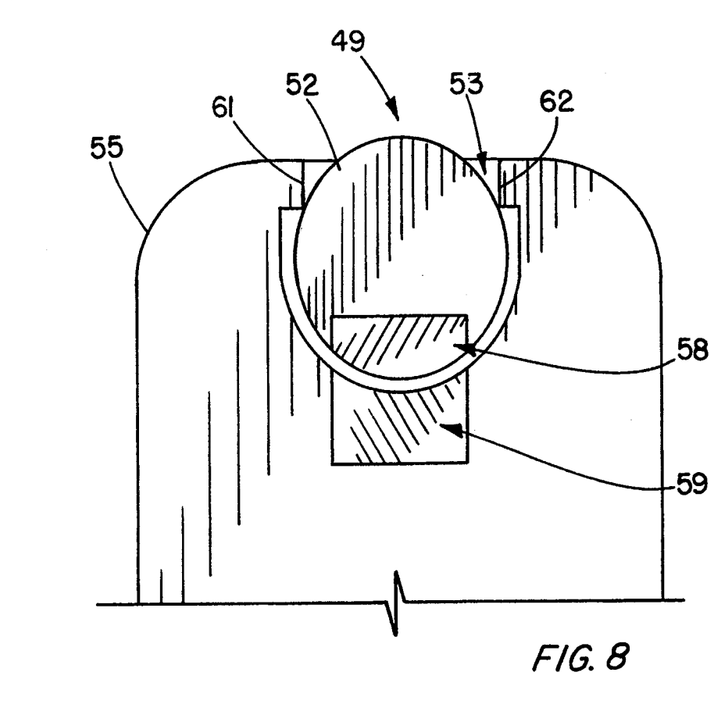
FIG. 8 depicts an end view of the connector body and lever of FIG. 7 taken along the line 8—8.

FIG. 8 depicts an end view of body 55 of connector 49 and lever 52 of FIG. 7 taken along the line 8—8. Lever 52 of connector 49 has no longitudinal recesses, but has a smooth outer surface that is pushed below and engages longitudinal projections 61 and 62 of channel 53 for maintaining the lever in the fixed position. End recesses 58 and 59 of the lever and channel, respectively, cooperate to provide for a convenient surface to engage the lever and push it out of the channel to a disengaged or movable position.

It is to be understood that the above-described drainage catheter is merely an illustrative embodiment of the principles of this invention and that other connectors, catheters, and drainage apparatus may be devised by those skilled in the art without departing from the spirit and scope of this invention. In particular, the distal end of the catheter may be preformed into any desired configuration for positioning and retaining the distal end of the catheter in any part of a patient's body. It is further contemplated that the flexible tension member may be attached in any one of a number of well-known ways to the distal end of the elongated member and drawable through one or more draw ports for positioning the distal end in the desired position. It is also further contemplated that the medical device of the present invention has application as an abscess or biliary drainage catheter, a nephrostomy tube in the renal pelvis, a gastrostomy feeding tube, or any other catheter requiring a distally positioned retention means such as a pigtail or loop. It is still further contemplated that any combination of longitudinal projections and recesses in or on the lever and channel or any other fixation arrangement can be used to maintain the lever in a fixed position. It is still yet further contemplated that the resilient material sleeve passage can have circular ridges or a spiral ridge formed therein to further grip and maintain the flexible tension member in a fixed position.

What is claimed is:

1. A lockable connector for use with a tension member in a drainage catheter, comprising:
   a body having a first body passage extending therethrough, a channel communicating with said first body passage, and a fluid seal positioned proximate said channel and sealing said channel from a fluid when said fluid is present in said first body passage; and
   a lever pivotally connected in said channel to said body and having a first end, a second end, and a cam surface proximate said first end, said body further comprising an opposing surface across from said cam surface, said cam surface having a locked position and an unlocked position, said cam surface when is said locked position for clamping a tension member between said cam surface and said opposing surface, said lever having a fixed position and a disengaged position for movement of said cam surface between said locked position and said unlocked position.

2. The connector of claim 1 wherein said fluid seal comprises a resilient material sleeve communicating with said channel for compression by said cam surface of said lever and having a sleeve passage extending therethrough and communicating with said first body passage and said channel for passage of a tension member therethrough.

3. The connector of claim 1 further comprising a second body passage having an external opening and communicating with said channel and wherein said fluid seal is also positioned in said second passage and comprises a resilient material sleeve communicating with said channel for compression by said cam surface.

4. The connector of claim 1 wherein said lever has at least one of a projection and a recess formed therein and wherein said channel has at least one of a respective recess and a respective projection extending into said at least one of a projection and a recess when said lever is positioned in said fixed position.

5. The connector of claim 4 wherein at least one of said lever and said body further comprises another recess formed therein in which said lever can be engaged to release said lever from said fixed position.

6. The connector of claim 1 further comprising a second body passage communicating with said channel and having an external opening for passage of a tension member therethrough.

7. The connector of claim 1 further comprising an elongated member for insertion into a patient and having a distal member end, a proximal member end connected to said body, and a member passage extending longitudinally therethrough and communicating with said first body passage, said distal member end being formed to be positioned into a desired configuration, and a tension member extending along said elongated member and positioned for drawing said distal member end into said desired configuration, said tension member having at least one end communicating with said cam surface.

8. The connector of claim 7 wherein said elongated member includes first and second ports proximate said distal member end and communicating with said member passage and wherein said tension member also extends through said first and second ports.

9. The connector of claim 7 wherein said tension member includes another end attached to at least one of said body and said proximal member end.

10. The connector of claim 7 wherein said fluid seal comprises a resilient material sleeve having a sleeve passage extending therethrough and communicating with said first body passage and wherein said at least one end of said tension member extends through said sleeve passage.

11. The connector of claim 1 wherein said channel further comprises a projection extending therein and proximate said cam surface when in said locked position.

12. The connector of claim 1 wherein said channel further comprises a projection extending therein and said cam surface includes a contour proximate said projection when said cam surface is in said locked position.

13. A drainage catheter comprising:
an elongated member for insertion into a patient and having a distal end, a proximal member end, and a member passage extending longitudinally therethrough, said distal member end being formed to be positioned into a desired configuration;
a lockable connector connected to said proximal member end and having a first passage extending therethrough, a channel communicating with said first passage, and a fluid seal positioned proximate said channel and sealing said channel from fluid when said fluid is present in said first passage;
a lever pivotally connected in said channel to said connector and having a first end, a second end, and a cam surface proximate said first end, said lockable connector further comprising an opposing surface across from said cam surface, said cam surface having a locked position and an unlocked position, said cam surface when in said locked position for clamping tension means between said cam surface and said opposing surface, said second end of said lever having a fixed position and a disengaged position for movement of said cam surface between said locked position and said unlocked position; and
tension means extending along said elongated member and into said lockable connector through said fluid seal for drawing said distal member end into said desired configuration, said tension means having at least one end extending to said channel of said lockable connector for communication with said cam surface.

14. The drainage catheter of claim 13 wherein said connector further comprises a second passage having an external opening and communicating with said channel, said at least one end of said tension means extending through said second passage and from said external opening.

15. The drainage catheter of claim 13 wherein said fluid seal comprises a resilient material sleeve compressed by said cam surface of said lever when in said locked position, and having a sleeve passage communicating with said first passage.

16. The drainage catheter of claim 15 further comprising a second passage and having an external opening and communicating with said channel and wherein said resilient material sleeve is also positioned in said second passage.

17. The drainage catheter of claim 14 wherein said lever has a recess formed therein and wherein said channel has a projection extending into said recess when said lever is in said fixed position.

18. The drainage catheter of claim 17 wherein at least one of said channel and said lever further comprises another recess formed therein in which said lever can be engaged to release said lever from said fixed position.

19. The drainage catheter of claim 13 wherein said elongated member includes first and second ports proximate said distal member end and wherein said tension means extends through said first and second ports.

20. A drainage catheter comprising:
an elongated member for insertion into a patient and having a distal member end, a proximal member end, and a member passage extending longitudinally therethrough, said distal member end being formed to be positioned into a desired configuration, said elongated member including first and second ports proximate said distal member end and communicating with said member passage;
a lockable connector having a distal connector end connected to said proximal member end, a proximal connector end, and a first passage extending therethrough, a second passage having an external passage opening, and a channel communicating with said first and second passages;
a lever pivotedly connected in said channel to said connector and having a first end, a second end, and a cam surface proximate said first end, said cam surface having a locked position and an unlocked position in said channel, said lever having a fixed position and a disengaged position for movement of said cam surface between said locked position and said unlocked position and having a first and a second recess formed longitudinally therein and a third recess proximate said second end in which said lever can be engaged to release said lever from said fixed position, said channel having a first projection and a second projection extending into said first recess and said second recess, respectively, when said lever is positioned in said fixed position;
a resilient material sleeve positioned in said second passage and through said channel to said first passage for compression by said cam surface of said lever and having a sleeve passage communicating with said first passage and said external passage opening;
a flexible filament means extending along said elongated member and through said first and second ports and positioned for drawing said distal member end into said desired configuration, said flexible filament means having a first end connected to at least one of said connector and said elongated member and also having a second end extending through said sleeve passage and from said external passage opening for communication with said cam surface.

21. A medical device comprising an elongated member having a distal member end, a proximal member end, and a member passage extending longitudinally therethrough, at least the distal member end being for insertion into a patient and means extending between the distal and proximal member ends and positioned and drawable for reconfiguring the distal member end into a desired configuration, and a lockable connector having a first passage extending therethrough, the lockable connector having a distal connector end connectable to the proximal member end of the elongated member, and a proximal connector end, a first passage extending through the lockable connector and communicating with the member passage of the elongated member; characterized in that said lockable connector comprises a channel communicating with the first passage, a fluid seal positioned proximate said channel and sealing said channel from fluid when said fluid is present in said first passage, and a lever having a first end and a cam surface proximate said first end, said lever being pivotally connected in said channel to said connector, said lockable connector further comprising an opposing surface across from said cam surface, said cam surface having a locked position and an unlocked position, said cam surface when in said locked position clamping said drawable means between said cam surface and said opposing surface.

22. A device according to claim 21, characterized in that said lever has a fixed position and a disengaged position with respect to said channel for movement of said cam surface between said locked position and said unlocked position.

23. The device according to claim 21, characterized in that said fluid seal comprises a resilient material sleeve communicating with said channel for engagement by said cam surface of said lever and having a sleeve passage communicating with said first passage for passage of said drawable means therethrough.

24. A method of percutaneously draining fluid from a cavity of a patient with a medical device comprising an elongated member having a distal member end, a proximal member end, and a member passage extending longitudinally therethrough, at least the distal member end being for insertion into a patient and means extending between the distal and proximal member ends and positioned and drawable for reconfiguring the distal member end into a desired configuration, and a lockable connector having first passage extending therethrough, the lockable connector having a distal connector end connected to the proximal member end of the elongated member, and a proximal connector end, the first passage of the lockable connector communicating with the member passage of the elongated member, said lockable connector further comprising a channel communicating with and sealed from fluid when said fluid is present in the first passage and a lever having a first end and a cam surface proximate said first end, said lever being pivotally connected in said channel to said connector, said lockable connector still further comprising an opposing surface across from said cam surface, said cam surface having a locked position, comprising the steps of:
    percutaneously inserting the distal member end of the elongated member into the cavity of a patient;
    moving the drawable means past the cam surface to reconfigure the distal member end into the desired configuration;
    clamping the drawable means between the cam surface and the opposing surface of the connector; and
    connecting the lockable connector to a fluid collection system.

25. The method of claim 24 further comprising the steps of providing a resilient material sleeve positioned in and communicating with the channel of the connector, the sleeve having a sleeve passage extending longitudinally therethrough and communicating with the first passage, and passing the drawable means through the sleeve passage, said cam surface when in the locked position compressing said resilient material sleeve to form a fluid-tight seal.

* * * * *